United States Patent
Herz et al.

(10) Patent No.: US 8,924,237 B2
(45) Date of Patent: Dec. 30, 2014

(54) DATABASE FOR PRE-SCREENING POTENTIALLY LITIGIOUS PATIENTS

(75) Inventors: Frederick S. M. Herz, Warrington, PA (US); Walter Paul Labys, Salt Lake City, UT (US)

(73) Assignee: Fred Herz Patents, LLC, Milton, WV (US)

( * ) Notice: Subject to any disclaimer, the term of this patent is extended or adjusted under 35 U.S.C. 154(b) by 1159 days.

(21) Appl. No.: 11/691,263

(22) Filed: Mar. 26, 2007

(65) Prior Publication Data

US 2008/0071578 A1 Mar. 20, 2008

Related U.S. Application Data

(63) Continuation of application No. 10/202,302, filed on Jul. 24, 2002, now abandoned.

(60) Provisional application No. 60/307,561, filed on Jul. 24, 2001.

(51) Int. Cl.
*G06Q 50/00* (2012.01)

(52) U.S. Cl.
USPC .................................. 705/3; 705/2; 705/4

(58) Field of Classification Search
CPC ...... G06Q 50/22; G06Q 50/24; G06F 19/322; G06F 19/327; G06F 19/321; G06F 19/325; G06F 19/328; G06F 19/3431
USPC ........................................................ 705/2–4
See application file for complete search history.

(56) References Cited

U.S. PATENT DOCUMENTS

| | | | | |
|---|---|---|---|---|
| 4,975,840 A | | 12/1990 | DeTore et al. | 364/401 |
| 5,159,180 A | * | 10/1992 | Feiler | 235/375 |
| 5,276,612 A | * | 1/1994 | Selker | 600/523 |
| 5,325,291 A | | 6/1994 | Garrett et al. | 364/401 |
| 5,471,382 A | * | 11/1995 | Tallman et al. | 600/300 |
| 5,752,237 A | | 5/1998 | Cherny | 705/4 |
| 5,852,808 A | | 12/1998 | Cherny | 705/4 |
| 5,875,431 A | | 2/1999 | Heckman et al. | 705/7 |
| 5,895,450 A | | 4/1999 | Sloo | 705/1 |
| 6,018,714 A | | 1/2000 | Risen et al. | 705/4 |
| 6,128,620 A | * | 10/2000 | Pissanos et al. | 705/2 |
| 6,272,471 B1 | | 8/2001 | Segal | 705/4 |
| 6,556,992 B1 | | 4/2003 | Barney et al. | 707/6 |

(Continued)

FOREIGN PATENT DOCUMENTS

WO WO 97/40460 10/1997

OTHER PUBLICATIONS

Tamar Lewin, New Weapon to Deter Malpractice Suits / Computer service helps doctors screen out litigious patients, Aug. 28, 1993, San Francisco Chronicle, p. A7.*

(Continued)

*Primary Examiner* — Sind Phongsvirajati
(74) *Attorney, Agent, or Firm* — Baker & Hostetler LLP (57) ABSTRACT

A database system stores information about potential patients that allows medical professionals to gauge the legal risk presented by the potential patients, giving the medical professionals the opportunity to avoid medical involvement with those individuals most prone to engaging in unwarranted legal actions. The database may also be used by insurance companies, legal services and other professional service providers to screen for potentially litigious customers. Information in the database is processed to provide a risk assessment score for each patient that is used for screening purposes.

19 Claims, 1 Drawing Sheet

(56) References Cited

U.S. PATENT DOCUMENTS

| | | | |
|---|---|---|---|
| 6,615,181 B1* | 9/2003 | Segal | 705/4 |
| 6,862,571 B2 | 3/2005 | Martin et al. | 705/4 |
| 6,901,404 B1* | 5/2005 | Bonutti | 705/311 |
| 7,366,676 B2* | 4/2008 | Evertsz | 705/2 |
| 2002/0095317 A1* | 7/2002 | McCabe | 705/4 |
| 2002/0143562 A1* | 10/2002 | Lawrence | 705/1 |

OTHER PUBLICATIONS

Laurence Hammack, Expert Testimony Provokes Mistrial Attorneys for Plaintiff Promise to Revive Allegations, Feb. 14, 1998, The Roanoke Times, p. B1.*

Rachel Emma Silverman, Litigious-Patient Database Shuts, Mar. 11, 2004, The Wall Street Journal, p. D6.*

* cited by examiner

DATABASE FOR PRE-SCREENING POTENTIALLY LITIGIOUS PATIENTS

CROSS-REFERENCE TO RELATED APPLICATIONS

The present patent application is a Continuation of U.S. patent application Ser. No. 10/202,302 filed Jul. 24, 2002, which claims priority under 35 U.S.C. §119(e) to U.S. Provisional Patent Application No. 60/307,561, filed Jul. 24, 2001, the contents of which are incorporated herein by reference.

FIELD OF THE INVENTION

The invention relates to a system and method for pre-screening potential users of professional services and products to identify those individuals that present a high risk of litigiousness.

BACKGROUND OF THE INVENTION

The need for modalities to curb the spiraling costs of professional services, which is driven in large part by expense related to legal costs and the cost of insurance protection against law suits, is widely recognized. This problem is disproportionately severe in the realm of medico-legal issues and is a major problem for virtually all providers of professional services and in the service industry, in general. In many cases, physicians are relocating, retiring or changing profession. Hospitals are curbing services at the cost of declining quality of care or are closing their doors, in many cases after over one hundred years of community care. Legal defense and extremely high settlements have created insurmountable debts. Similar high cost of client-initiated law suits are impacting virtually all professions. Thus, the need to avoid litigious clients and situations is obvious and identification of multiple client and situational factors by a system which enables professional service providers to pre-screen and identify clients who have a greater than average potential for initiating law suits is important in order to minimize the ultimate risk of litigation against the physician as well as other professionals.

SUMMARY OF THE INVENTION

A database system is described that allows medical and other professionals to gauge the legal risk presented by new patients/clients, giving them the opportunity to avoid medical involvement with those individuals most prone to engaging in unwarranted legal actions. In this way, such efficient knowledge dissemination ultimately provides the physician with means for avoiding or reducing the risks of liability litigation through patient motivated medical malpractice suits before the fact by enabling him/her to make much more intelligently informed decisions regarding such questions as acceptance of that patient or conversely, denial of the associated needed medical services to that given patient (or acceptance for particular types of medical services or treatments) as well as to what degree is special medical attention and/or personalized care directed to the emotional needs of the patient most significantly warranted in order to minimize the ultimate risk of litigation against the physician eventually resulting from that patient. Information within this system will allow improved physician-patient matching. Other applications of the present system pertain to hospitals, insurance companies, legal services and other professional service providers. For example, using the information by the disclosed system will enable insurance carriers to more appropriately prorate individual premiums based upon more accurate evaluation of risk profile.

DETAILED DESCRIPTION OF ILLUSTRATIVE EMBODIMENTS

1. Problem

Many of the physicians practicing in urban or suburban areas (representing perhaps 50% or more of the total population in the US), and particularly those practicing in urban areas in the northeastern United States, have a high probability of facing egregious medical malpractice suits. Whereas an estimated 95% of patients are essentially non-litigious, with regards to physician medico-legal liability issues, it is felt that a mechanism to identify the small percentage of those patients who are litigious is desperately needed. Certain specialties are especially predisposed to medical malpractice claims. Some of the most vulnerable include obstetrics, neurosurgery, vascular surgery and pediatrics, although there is an increasing incidence of lawsuits across all surgical specialties. In many cases physicians are leaving the practice of medicine or relocating to avoid geographic areas with higher than average rates of medico-legal action and unreasonably high damage awards. Hospitals and other medical establishments spend large amounts of money and personnel effort in defensive countermeasures, since frivolous lawsuits affect their ability to properly subsidize the delivery of quality health care, as well as their ability to locate new doctors locally. These factors are a major cause of the spiraling out of control costs of medical care, which directly impacts government, industry and finally economic well being. Parallel problem situations are impacting paramedical services, non-medical professional providers, insurance carriers, and even the legal service providers themselves. The same type of system as described herein can be used in parallel to the system described in preemptive measures to avoid the litigious client or situation in non-medical applications.

2. Proposed Solution

The present service substantially addresses this major problem by enabling physicians to pre-screen potential patients for greater than average litigiousness. The system consists of a computer database, accessed either on a per-use basis or as an add-on to standard practice management software, and computerized patient registration systems, into which the medical professional enters the patient's name, address, and social security number and other demographic data. The system uses a stored history of medical lawsuits (among other data) in combination with statistical algorithms to generate a score. Much like the credit scores used by loan officers to gauge an individual's likelihood of default, the score generated by this system gives the medical professional a quantitative basis for assessing the risk that a given patient will engage in frivolous litigation. If the risk is too high for the professional's preference, he/she can choose to not establish a medical relationship with the patient, which is the practitioner's legal right. The present system is similarly applied to non-medical service providers using the above array of data to determine the client or situation with the greatest potential for lawsuits.

Figure 1:
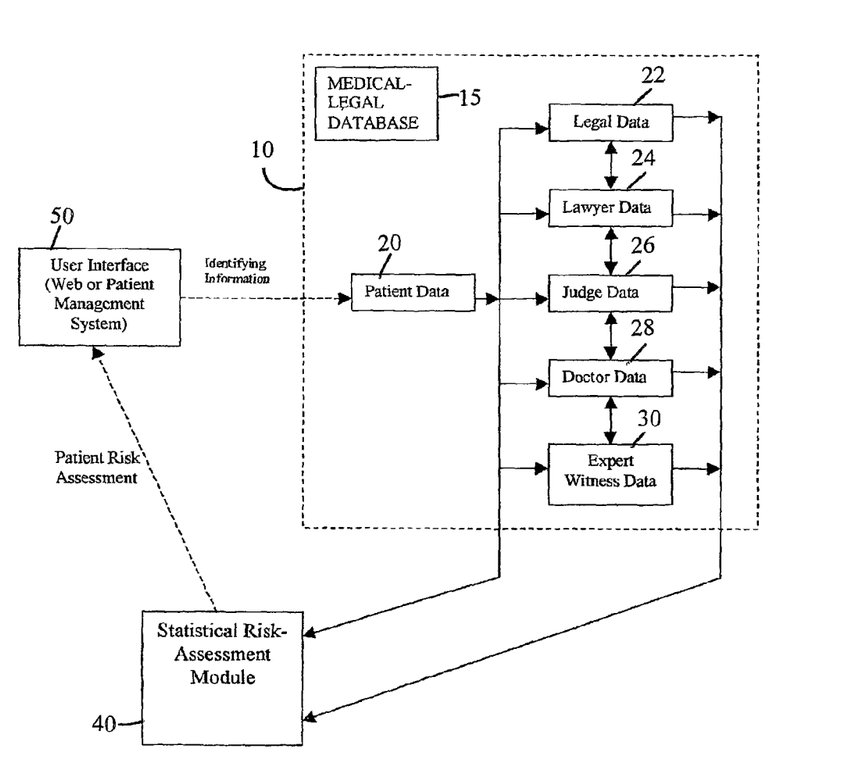
FIG. 1 illustrates the use of the litigious patient screening system of the invention whereby a user transmits information about the identity of a potential patient either manually (through a web interface) or automatically (through patient management software) and this information is then fed through a system that (1) matches the patient to a database (linking the individual to other doctors, past lawsuits, related lawyers, etc.), and (2) uses a statistical model to predict the likelihood of litigation and expected cost any such lawsuits. This risk assessment is then transmitted back to the user, and is either displayed on a web page or entered automatically into the office system, depending on the mode of initiation.

FIG. 1 illustrates the system for screening for potentially litigious patients in accordance with the invention. As illustrated, a database 10 includes a medico-legal database 15 and a collection of patient data 20, legal data 22, lawyer data 24, judge data 26, doctor data 28, and expert witness data 30 that is processed by a statistical risk assessment module 40 to provide a score as described below. The calculated risk assessment for the patient is provided back to the user through a user interface 50, such as a web or patient management system that also enables the user to input identifying information for search purposes and/or database storage for future use.

3. Database Organization

The creation of the relational database 10 supporting the patient tracking system would be complex, in that many different sources of legal data would need to be compiled; however, the technical aspects of the database itself would be quite straightforward. It would simply contain records on the identities of patients (20), doctors (28), expert witnesses (30), lawyers (24), and judges (26). Each record would contain various forms of medical, legal (22), and demographic information, as well as links to other patients, doctors, expert witnesses, lawyers, and judges.

In particular, the patient records 20 would include:
Links to family members
Medical history (including health status and doctors previously seen)
Socioeconomic status
Demographic information (including age)
Record of the nature of previous disease (by standard code number) processes and the timing of the disease(s)
Current disease(s)
Family history of disease(s) and proximity of blood relationship to patient
Nature of disease (litigious disease process) for which definite degrees and medical malpractice cannot be proven or disproven objectively and conclusively (e.g., back pain, thoracic outlet syndrome, certain neuropathies, emotional trauma such as that associated with suffering, intractable pain syndromes)
Evidence of instability such as mental records, criminal background, evidence of previous courses of medical treatment not followed (checking out of hospitals by signing out against medical advice, not following prescription plans, present and historical subjective level of fear of receiving treatment, in general, or of the present condition, etc.)
Previous litigation history ((including medico-legal and non-medico-legal as well as suits initiated by the individual and those brought against the individual by a third party (e.g., were the suits of a medico-legal nature, were the suits egregious or most likely unjustified such as summary judgments in favor of the defendant)
number of suits (total)
number of suits of a medico-legal nature
types of suits
doctors, lawyers, and expert witnesses involved
money demanded
suit outcomes
Does the patient have a history of initiating suits, which are eventually dismissed or consist of frivolous lawsuits?
The patient's history of initiating (or his/her immediate family) medico-legal suits (such as number of suits initiated and awards or settlements recovered)
Does the patient have a history or suspected history of feigning injuries or illnesses?
Does the patient have a history or suspected history of committing medical or disability insurance fraud?
Doctor records 28 of referring physicians (typically belonging to other doctors) would include:
Educational/professional profile
Patients seen
Commendations or condemnations by medical boards and organizations (including hospital review boards, state medical organizations)
Physician ratings services
Number of malpractice cases already faced, with outcomes and amounts
Demographic information
Lawyer records 24 would include:
Educational/professional profile
Commendations or condemnations by legal boards and organizations
Lawyer ratings services
Number of cases won/lost/dismissed
Aggressiveness of solicitation (does lawyer "chase ambulances" or only take on valid cases?)
Does lawyer have a history of initiating lawsuits which are eventually dismissed or consist of frivolous lawsuits?
If so, what is the lawyer's history of success in this regard?
Demographic information
Involvement with patients, doctors, and judges
Degree of public notoriety (extracted from on-line media)
Judge records 26 would include:
History of cases seen
Commendations or condemnations by review boards
Degree of public notoriety (extracted from on-line media)
Expert witness records 30 would include:
Educational/professional profile
Demographic information
Case involvement
Overall success
Degree of public notoriety (extracted from on-line media)

4. Implementation and Algorithms

Simply put, the function of the statistical risk assessment module 40 is to receive as input identifying information about a patient (e.g. name, address, social security number), and to return a value representing the predicted litigiousness of the given patient, such as the probability of a lawsuit as a result of treating the present condition as well as predicted dollar amounts of any ensuing lawsuits and a breakdown which correlates predicted probability with ultimate monetary recovery by the plaintiff:
a. In general as an overall probability statistic; and
b. If litigation were to ensue.

The system could also reveal the effect that such a law suit would have on the physician's insurance premiums, and if these premiums are adjusted in accordance with the physician's adherence to avoiding certain levels of litigation risk via the present system, what would be the direct consequences on the physician's insurance premiums for:
 a. Accepting the present patient, and
 b. Accepting other patients within the same approximate risk level of the present patient based upon the litigious risk statistics of the physician's other patients. The system could even provide a break down of what the direct monetary losses would be in this regard for accepting the patient compared with the likely direct monetary gains that the physician would achieve for accepting the patient for his/her present condition as well as analogously what the comparative long term effects would be on direct income from accepting other patients at a similar risk level compared to the anticipated losses sustained as a result of insurance premium increases resulting from accepting this similar higher risk segment of the physician's current typical population of patient candidates, and this value could also be adjusted in the event that litigation did occur in accordance with:
 1. The estimated associated probability thereof as at the average predicted plaintiff recovery under the present conditions, and
 2. The predicted probability/plaintiff recovery distribution based upon all of the relevant variables of the present type of circumstances (e.g., likely patient condition, general health, litigiousness factors, etc.).

In the preferred embodiment of the system, the service is bundled with a practice management system 50, which maintains persistent connections to a central database of medico-legal information. In particular, when the receptionist in the physician's office, clinic or hospital (directly or over the phone) enters patient information after a patient signs in or schedules an advanced appointment, the system automatically queries the database remotely and instantaneously delivers the litigation risk profile. Examples of such practice management systems include WebMd (www.webmd.com), CitX's IntramedX Practice Management systems (www.intramedX.com) and InfoCure (www.infocure.com).

In other variations, the physician could pay by the patient or alternatively according to a flat fee allowing use of the system for a set period of time (e.g. $100/month). In this case, the interface could be through a web page, eliminating the need for any extra equipment on the part of the physician. In this way, a trial version of the software could even be downloaded to the physician's practice management system (e.g., for x days free). Moreover, there is an additional service for physicians, which is described in co-pending patent entitled "Physician's Referral Network". This service enables physicians to make referrals to one another based essentially upon barter currency, which is transacted in conjunction with the referrals. The present system may be used to provide an additional screening function for the referrals made via the present approach.

Internally, the system statistically analyzes the previously-described variables, using standard descriptive data mining techniques to determine the degree of relevance of each associated variable in predicting the likelihood of further future litigation based upon past behavior. The receptionist or physician may also enter data relevant to the condition of the patient such as the general impression of the patient's overall present state of health or (for the physician exclusively), the patient's symptoms, complaints, likely diagnosis or potential diagnosis (such as if the diagnosis is potentially associated with a severe condition) this information can, in turn, be used to predict the likely disorder(s) (which could even be broken down by the physician as a probability value) and its severity; the likelihood of complications from the disorder (essential precursor of litigation) as well as (in many cases) the likely ultimate treatment protocol and its associated likelihood of complications (another essential precursor of litigation) are thus factored into the system's calculations.

EXAMPLE

There are obviously a multitude of ways in which the predictive model could be developed. This example shows one of many possible approaches:

First, a large database of patients is scanned for defining examples of "litigious" or "non-litigious" patients. In the first case, any patient linked with a criminal record of legal fraud, or who initiated two or more medical malpractice lawsuits that were subsequently dismissed because of insufficient evidence, will be considered a very high litigious risk. In the second case, any patient who has undergone major levels of medical care (e.g., over $50,000 or over 5 procedures in the last 10 years) without ever involving a doctor legally will be considered a very low litigious risk.

A set of explanatory vectors is then prepared, containing all available data linked to the patients selected as being very high or very low risks. For example, for each patient i we could define:

$$Xi = \{xi1, xi2, xi3, xi4\}$$

Where:
 $xi1$=dummy variable (0/1) representing association with Lawyer A.
 $xi2$=dummy variable (0/1) representing association with Lawyer B.
 $xi3$=Income level.
 $xi4$=Age.
And we could also define Yi, where:
 $Yi=1$ if patient is very litigious
 $Yi=0$ if patient is very un-litigious
In this case, the model will be structured as a logit regression (a type of linear regression that, while fed with a range of data, returns an output value ranging between zero and one).

$$Prob(Y=1|Xi,B) = \exp(B'X)/(1+\exp(B'X))$$

Where B=beta, a vector of coefficients that is estimated on the previously-described data set. The model will therefore assign a higher probability to Y=1 when B'X is large.

Suppose the resulting coefficients are as follows:
 B={10, −10, 1}. This indicates that Lawyer A is not associated with either type of patient (indicating a fairly neutral lawyer), whereas Lawyer B is strongly associated with litigious patents. Moreover, a high income is linked with those patients less likely to sue, whereas age does not have much impact (although its small positive value indicates aged patients are mildly correlated with litigation).

Now, when operating, the system will operate in two stages. After patient identifying information has been provided for patient Xj:

Stage 1: Rule-based filter: Does patient Xj fit into either the highly litigious or highly non-litigious categories, as previously defined? If so, simply return a litigation probability of zero or one.

Stage 2: Statistical Model. Using the previously-calculated value for coefficient vector B, calculate $\exp(B'Xj)/(1+\exp(B'Xj))$—this will be a value ranging between zero and one, indicating the likely litigiousness of the patient. Note that vector B is multiplied value by value into the patient's data vector, which allows all the different factors to be taken into consideration. Thus, even if the patient is somewhat aged, a high income and association with Lawyer A will push the overall score down, indicating the patient is a low risk venture for the physician.

The system could be further enhanced through the offering of supplemental medical malpractice insurance: if the physician uses the present service and does not accept patients who fall above a certain probability value for litigation (verified by a secure agent associated with the physician's billing software), the insurance would cover any claims over and above those covered by standard malpractice insurance policy and the physician's CAT fund. In a variation, the present system could actually be used as a lower premium version of the CAT fund. The present service could even be used as a reduced premium form of the physician's basic medical malpractice insurance in which premiums arc set based upon the system's predicted litigation-based monetary risk to the physician. It should be noted that the system incorporates those variables already used in standard medical malpractice actuarial models. Thus, the present service could incorporate an extended version of the service for those physicians who are interested in lower medical malpractice insurance rates, e.g., as part of a special policy for users of the system who follow certain recommendation criteria. One novel business model, in fact, could even involve the creation and development of a special new insurance company, which is developed entirely for physicians who incorporate the use of the present system (in which case, it would likely be implemented as a proprietary system).

5. Data Sources and Collection

Several important issues must be considered in the design of the present system. One of these relates to the means for collecting and updating the data, which is provided to the system. It is important to first determine whether and where the desired data exists in digitized form (or, if not, it may be necessary to access it and enter it into the system via manual means, (e.g., from court house records)). There are a variety of services available in which it is possible to access on-line databases (for a fee) which contain considerable personal information about individuals. Such databases particularly in aggregate may contain a history of such individuals. Legal databases containing case histories for legal professionals may also provide a useful resource, as would any available on-line county courthouse records, which happen to be stored in database format. A very important aspect of the above is given the potentially variable heterogeneous data formation, it is important to enable each of the various heterogeneous database formats to be able to communicate with each other. This requires translation software, which is specific to each type of heterogeneous database software. In many cases, the software itself must be further customized to each individual database to the extent that it has certain uniquely definable characteristics.

Sources of data might include:

a) Standard legal databases, with names of plaintiffs and defendants involved in medical litigation.

b) Court transcripts, which would include such further details as the names of expert witnesses. One potentially valuable data aggregation of this information is a commercial vendor called Knowledge X (www.knowledgeX.com) which contains complete legal database information as well.

c) On-line news sources, such as those provided by Nexis/Lexis. Natural language processing techniques could scan these databases of news stories for evidence of past medical litigation. Once a candidate story is located, the names of the defendants and plaintiffs could be searched for in tandem, such that the eventual outcome of the case (settlement, trials, dismissal by the court, etc.) could be noted. Court cases which involve the dismissal of a plaintiffs case would be of special interest, as the plaintiff, lawyers, and professional witnesses involved would be suspect.

d) Medical board records, which would provide the names of doctors either being commended or condemned by other doctors under various circumstances.

e) Information from the National Data Bank to the extent that it is available for access by the present service. This should also include the physician's entered response to the allegations of medical malpractice or practice restrictions which are recorded within the Data Bank.

f) On-line and printed legal advertisements. The names of lawyers observed being overly aggressive in their solicitation of malpractice cases could be recorded. In other words, certain lawyers would be flagged as "ambulance chasers", and patients who are also clients of those lawyers (or likely to become clients, given their locale), would experience an adverse impact on their score.

g) Insurance records. These would hold evidence of previous lawsuits, and would be useful for linking family groups.

h) Medical records.

i) Demographic and income databases.

j) Courthouse records.

Additional Potential Applications

1. Incorporation into Patient Referral Forms

The information used in the present prescreening process can readily be incorporated into the current mechanism widely used by managed care specialty referral forms. In this case the Health Maintenance Organization (HMO) would implement the use of the present system to screen patients being referred to specialists for specialty medical services. The issuance of the patient referral form by the HMO would then also be subject to medico-legal clearance via the above system and this information would be entered directly on to the existing patient referral form as an additional prerequisite for HMO approval of the referral.

It is worthy to note that this additional HMO screening of patients according to degree of litigiousness would put additional pressure upon the referring physician to implement the present system, in order to insure that their patients who need quality specialty care are able to receive it subject to referral approval by the HMO. Thus, it is certainly conceivable in this scenario that patients who are likely to be very litigious, who are accordingly screened out by the HMO and denied medico-legal clearance for referral, are likely to need a higher premium form of insurance provided either by the same insurer or by a separate high risk specialty insurer (as described below). It is also worth noting that highly litigious patients are likely to become apparent to employers who offer insurance benefits through group plans to their employees inasmuch as they will typically not pass the initial application level screening by the HMO for that group plan policy. Moreover, in such cases employers may further consider employees who are high risk from a medico-legal litigiousness standpoint to also be high risk for potential litigation against the present prospective employer who may, in turn, consider not hiring that employee. Accordingly this propensity on the part of employers could readily become a further dissuading factor for patients to sue physicians in the first place.

2. High Risk Premium Patient Insurance

It is entirely plausible to assume that HMOs would implement the present system to screen patients at all levels of HMO patient approval, i.e., at the time of application for enrollment, the applicant would, of necessity, have to be approved through the system as implemented by the insurer. Both primary and secondary (or subsequent insurers) may wish to independently implement the present system for purposes of assuring that the proper screening has occurred and because each insurer is likely to have differing criteria for acceptance, rejection and associated premiums categories. In this way, the actuarial formula of the insurer may incorporate additional attributes which are relevant to overall medico-legal litigation risks instead of purely medical data alone, i.e., predicted patient litigiousness in addition to present and past medical conditions such as those attributes detailed within the present invention. In addition, the present improved actuarial model may also be used for patient insurance renewal in the same fashion as is used in the patient application process. Unless regulatory agencies place restrictions on which types of variables related to the patient (and to what degree) these variables can be used in determining insurability and premiums of the patient, the same revised actuarial model which incorporates the attributes of the present invention in order to determine over all litigation risk for purposes of insurability and rate setting should also be used for HMO approved medico-legal clearance referrals. Of course, rejection of the referral would have to be superseded by a doctor's judgment if the case is determined to be a medical emergency. For patients who are considered "high litigation risk" the insurer, instead of denying insurance coverage altogether, the insurer may, at the application stage, or at the insurance renewal stage, in many cases place the patient in a higher risk category (for which there may be multiple high-risk categories). Another insurer who specializes in high-risk insurance may be available to provide coverage for those cases which do not pass the acceptance criteria of standard HMOs. Thus, a higher premium form of insurance whether provided by a specialized carrier or as a higher risk category of the standard insurer would have to be provided by the primary insurer and probably by the secondary and tertiary insurer as well.

3. Minimizing Medico-Legal Risk by Optimizing the Appropriateness of the Match between the Physician and the Patient.

Although the primary goal in minimizing the chances of medico-legal litigation is to initially and preemptively screen out the highest risk patients for litigation, there are additional measures that can be taken to additionally MINIMIZE the overall probability of encountering ultimate medico-legal liability issues. In particular, it would be in the interest of hospitals and clinics to be sure that once a patient has been appropriately screened for an unnecessarily high degree of litigiousness, to be sure that there is also a good match between the patient and the physician based upon the specific detailed initial complaints and symptoms (as well as medical history) which together would be suggestive of the likely type of disorder or system involved which could be valuable data for purposes of improving and, in turn, optimizing selection of the physician(s) who based upon their specific skill sets and the associated clinically demonstrated proficiency thereof would be most appropriately suited for that particular patient. Accordingly, such an approach further ensures that physicians who are not optimally (or at a minimum not adequately) skilled and proficient with regards to certain system disorders, disease processes (or even diagnoses) which are likely to be associated with the present patient symptoms and medical history actually do not ultimately treat the patient (notwithstanding emergency or other potential extenuating circumstances). Currently, the standard protocol by which certain physicians have rights to perform certain procedures is very crude and is based upon each individual "delineation of hospital privileges" (or commonly known as "hospital privileges"). Within its own particular venue, each hospital has the inherent right to dictate which particular medical procedures and treatments (delineation of privileges) are performed and by whom. Typically, the chief of each department is assigned the responsibility of determining this delineation of privileges for each physician practicing at that hospital under his/her jurisdiction. However, this approach unlike the aforementioned which is herein proposed is often based largely upon subjective opinion and is often even influenced heavily by politics which occur internal to that specific hospital. Moreover, in accordance with the presently accepted protocols, there is no consideration whatsoever given to the unique physical conditions and associated medical history of the patient or whether the physician has specific medical knowledge or expertise which matches these medical profiles of the patient. There is thus a substantial and unrecognized need in the attempt to further reduce medico-legal risk for a more sophisticated scheme which applies detailed knowledge of each patient including present condition(s) as well as past medical history and family history in combination with a detailed history of each physician's experience and the associated success and shortcomings related to this experience. Typically review of delineation of clinical privileges occurs only every two years on cursory review of a department chief. There is currently little objective physician volume/success data available for review in granting clinical privileges. Data presently available is incomplete and, in most cases, no data is available nor is it requested at the time of the review and granting of clinical privileges. Hospitals and regional medical societies will have available internal data banks which will represent an ongoing evaluation of all physicians and all disease processes treated in respect to staged severity of disease and in respect to success/failure rate (which is relative to this determined staged severity of the disease) on a case-by case basis as well as category specific, case type specific (predictive success/failure rate for any given newly introduced or developing case), and overall success/failure rates. Variations of the present statistical algorithm as above described will be implemented to calculate from this data the optimum predicted conditions of physician and medical practice and/or medical center for optimum treatment of each patient. It will include complete medical practice history of all physicians subscribing to the service such as success/failure statistics, complete litigation history, etc. and other variables as described above. Particularly valuable attributes for medical centers, hospitals and clinics may include the profiles of the physician who would be treating the patient (typically a specialist in referral cases), the profiles of the other physician(s) who would be (or would likely be) treating the patient (either for other specific medical care or the likely attending physician), general quality ratings or reputation of hospital support staff, medical testing and treatment equipment and facilities which are relevant to the patient's medical needs and their associated quality and degree of overall importance to the patient's present medical needs.

This statistical algorithm will also determine which point in the progression of the medical status, as well as which point in the treatment process is the most optimally appropriate circumstances to refer the patient to another physician or medical center, in as much as the present statistical algorithm is able to consider both where an optimally suitable physician for the present medical status of the patient is located as well as consider where the most opportune medical support staff is located, as well as other relevant attributes such as more subjective aspects of this algorithm such as the appropriateness and quality of the testing and treatment equipment available at the center as well as to determine the quality of the staff overall. Regional and personal financial interests and political considerations must be set aside in deference to objective optimum patient care. As a result of the predictive nature of the use of the present algorithm in a data mining application, somewhat more subjective data will be gleaned from the algorithm which will efficiently direct educational and training resources to determine which geographic and specialty areas to emphasize for training programs by determining the relative distribution of trained medical specialists in each specialty area. Ideally, such an algorithm would incorporate longer term predictions based upon such data as predicted demographic changes, anticipated technical advances in each field (determining the relative need for newly trained professionals) as well as present staff admissions and areas of training emphasis of other hospitals, clinics and teaching medical centers and the emphasis and profiles of regional independent medical practitioners (which would be indicative of type and quality thus effective competition for referrals by the present system on a given locality basis).

The present system would be of considerable interest to hospitals, insurance companies, clinics, or private practitioners. For example, hospitals may use such a scheme as an improved model for approving, denying or redirecting physical referrals to other doctors. It is of value to apply the same basic data model as described above in order to accurately predict the associated risks of complications for each patient (and with this data determine the medico-legal risks by also considering the patient's degree of litigiousness) based upon that physician's history of clinical treatment to other patients who are most similar to that of the present one. The statistical algorithm could, for example, determine across a large data set of physicians and patients which key features of the physician are most predictive of success (thus ultimately non-litigation) for that particular patient's medical status.

Physician data sources include those relevant ones to physician quality and expertise such as physicians training and history of cases performed (which historically is data submitted to the hospital by the physician) including, of course, most relevantly how many of the same types of cases were seen and the percentage of those treated which were successful cases. This data should also include the litigation statistics. The information relating to the patient is available through similar sources.

Typically such detailed patient data is available through digitized hospital records, insurance data bases, physician medical records such as patient charts (including practice management databases) and other data detailed above.

Some of these patient records would include present medical status and conditions, medical history, medical history of family members and previous litigation history.

Patient data includes court transcripts and legal databases as well as a variety of other data sources such as those described above. It is important to note that physician data not only incorporates attributes representing qualitative data indicating the type of experience (degree of similarity of the experience to that of the patient's present medical status which is currently being presented) and quantitative data (number of previous cases seen which are of a relevant nature to the present one) but also the relative degree of overall success in treating the relevant patients seen and overall relative degree of success for all patients previously treated overall, where relative degree of success may be a numeric percentage score of how the present physician's success compares historically as a ratio to other physicians on a given similar case by case basis which is, of course, in turn, averaged overall for each physician. "Success" may be determined by such variables as nature and severity of complication and morbidity as well as mortality rates and subjective assessment by the physician during past treatment cases and follow-up visits. Medico-legal activity may be another useful variable provided that these actual statistical values are normalized by the predicted degree of medico-legal litigiousness of the patients which actually sue and in this statistical model details of the nature of the medico-legal complaint are considered as well as the ultimate outcomes of the suits. Effectively, a matching score between the physician and the patient is calculated as well as that of the other physicians who are also presently viable alternatives to the present physician. For purposes of hospital clinic or physician specific implementation, a number of rules for example could be constructed automatically or manually based upon data analysis of overall success/failure rates for various types of physician/patient statistical correlation. For example, as a physician/patient matching score (below X may not be suitable under any circumstances notwithstanding emergency, etc.). On the other hand, if another available physician presently is (or becomes) higher than the present physician presently treating the patient and this amount exceeds the score by amount Y (or amount Y if the present physician's score is at or above not unacceptably low (however, nonetheless sub-optimal) score within range Z), the patient could be instead referred onto another physician who is better or more specifically experienced with regards to the patient's present medical needs. Geographic variables could also be incorporated into such rules as well as such factors as the degree of the matching score of the hospital staff (if relevant) to that of the patient's needs.

Medico-legal pressures and insurance company pressures will represent the primary motivating factors which will compel the medical providers to adapt the presently described protocol. As a result, it is anticipated that one potential consequence of wide spread use of the present system is that very qualified physicians and particularly qualified and focused specialists are likely to receive a large number of patients via the present system. The same is true of very high quality medical centers such as those with a particular medical focus and emphasis. As such, it is likely that such a resulting quality based demand scenario, once it emerges within the healthcare field, will drive such high quality primary physicians, specialists, clinics and medical centers to not only preferentially select patients of low liability risk but also those who are able and willing to pay independently for higher quality healthcare (in addition to or even independently of HMO coverage). Those who are able to still justify some of their services to be paid by medical insurance may offer certain routine services while also providing premium services for an additional fee which is charged at a higher rate than insurance would cover (that is if it would even cover it in the first place). Moreover, it is likely in this scenario that extremely high demand physicians, clinics and medical centers may offer services exclusively at a rate which requires additional fees to be covered by the patient directly for the care of a surgeon, preferentially select those patients who appear to require complicated, unusual or lengthy surgical procedures as well as those who are willing to pay for non-HMO covered specialty treatments such as preventive treatment and therapeutic regimens and also patients who choose to pay for non-HMO covered diagnostic tests involving advanced technology, technical skills and equipment. Because the types of treatments which a physician offers patients affects litigation risk, the optimum price which the physician should charge for each treatment is influenced by overall demand of the patient population (more particularly the segment of the potential patient population which the physician actually provides that particular treatment for) as well as litigation risk of that patient population being treated. This value may be determined by an optimization technique which is designed for this type of multi-variable problem techniques are well known in the field of statistics.

In certain cases in which the decision as to the most appropriate treatment regimen is not entirely clear cut or is of a somewhat subjective nature, because certain risks or some complications associated with each potential treatment regimen (as well as the risks associated with resulting litigation) will tend to be different, the system may provide the physician with a comparative predicted estimate of the various risks associated with this potential for resulting litigation for each relevant additional treatment regimen. Using optimization techniques, the present methodology may also be also tailored to identify an optimal relative volume of different kinds of patients, based on the size of the pool of potential patient selection available to the physician (which is a function of litigation risk probability and probability/potential for monetary profit which are also subtractive variables). The optimization technique may also use data from numerous other physician's billing systems in order to predictively suggest this optimal volume distribution of different patient types (and ultimately treatment types). In light of attempting to achieve an optimal price (for optimal profitability) the physician may wish to charge for these non-HMO covered (or patient supplemented) medical services in order to optimize for example, likelihood and degree of profitability or to optimize this value while also maintaining risk of litigation of the type which could harm his/her practice within an acceptably low level such that long-term probability and degree of profitability is optimized. In an analogous application HMOs within reasonable or regulatory limits may wish to set rates for certain treatments based upon the same types of variables. It would even be possible to adjust premiums based upon consideration of the variables associated with which patients are actually treated and which treatments are actually given to those patients. This approach would further incentivize the physician to choose to accept those types of patients who are not only the most profitable in light of their overall low risk of litigation as well as those treatments which represent the lowest risk of litigation and the highest returns from a profitability standpoint. Because the profitability potential of certain treatments (and on perhaps certain types of patients) may represent a different (in some cases opposing) long term monetary value for the physician compared with that of the insurer, it may be in the insurer's best interest to adjust for this factor by setting the rates, e.g., by further accentuating the cost of premiums for those treatments which are not only higher risk but also higher profitability potential for the physician.

At a more general level, the presently described scheme embodies a profound paradigm shift which would indeed represent a much more efficient commercial model for healthcare which is quality-market driven largely exists as the pro-quota for most other industries within capitalist countries. Moreover, it is worthy to note that the mere introduction of the present system will drive the further and ongoing demand for its use in health care.

For the implementation within HMOs, the present physician/patient appropriateness score could be the most accurate model for determining HMO based medico-legal clearance for patient referrals as described in sub-section 1 within the present section (in as much as a very accurate determination of medical risk is factored into the overall medico-legal liability prediction scheme and finally the physician/patient appropriateness matching score is likely to be an extremely valuable metric in malpractice actuarial models used by HMOs for use in the approval of policy renewal procedures and as well as risk category allocation for the patient.

Similarly, this matching score between the patient and the prospective physician is an appropriate additional variable to be added to the HMOs algorithm used to determine medico-legal clearance for referral of the patient to a particular identified specialist, and if the matching criteria is inadequate or even sub-optimal, the present system may recommend another local physician who is more suitable for that particular patient (e.g., is on the same hospital staff, or has associated hospital privileges) or for non-hospital patients such referral recommendations by the insurer (or physician for physician practices or clinic) could be based upon locality including degree thereof using zip code information of the patient based implementations compared to office or hospital locations at which each physician practices. It should be noted this particular approach would be ideal for a large scale automated referral system which is described in co-pending patent application entitled "Physicians Referral Network", in as much as a very large pool of physicians with profiles of expertise available via the network and at any given relevantly required physical locality or hospital.

4. Commercial Marketing

Certainly, there are useful applications of the present system to commercial marketing. Hospitals, HMOs, physicians, clinics, pharmacies and pharmaceutical companies spend billions of dollars per year on consumer advertising. For example, areas which have a high degree of litigiousness based upon demographic data should be weighed against the profit opportunity of those areas minimizing a market campaign by geographic area. In the case of pharmaceutical companies in particular, litigation is a major problem, however, the litigation predictions generated by the data model would, of course, be for litigation against the drug maker and some slightly different variable may be important compared to predicted litigation against health care providers (although not to minimize the potential relevance of litigation history, particularly against health care providers). An example is, the likelihood and likely degree of severity of health risks and potential harm to the patient associated with a drug. This may include, of course, anecdotal evidence such as chemical and biochemical similarities with the nature and physiological actions of the drug (respectively) as well as (if available side effects and health problems associated with preliminary trials on humans and animal studies as well as if the drug has already been released commercially) the documentation of medical side effects, complications and mortality regarding their numbers and all variables associated with rates of occurrence as well as (importantly) completed litigation history. Accordingly, targeted direct marketing via marketing database lists are also an important form of advertising for each of the above commercial categories. The present system would be usefully employed as a tool for screening out those individuals and households, which are demonstrated or predicted to have litigious propensities.

The present invention for screening litigious clients is certainly extensible into other paramedical and non-medical professional domains including but not limited to legal services, financial planning and advisory services, tax advisory services, stock brokers, investment brokers and dealers, and engineering firms. In these alternative professional domains for which the present system may be adaptively modified, it would be obvious to the artfully skilled reader that the features as applied to physicians for purposes of predicting future probability of litigation for a given service to a particular user can be appropriately applied to analogously similar features which are, however, instead relevant to the specific professional domains of the particular professional service provider (e.g., professional credentials, previous litigation for particular types of services rendered, etc.).

The present system could also be used by employers to screen potential employees for litigious propensities. In this latter example the general inherent risks for monetary loss to the employer associated with ultimate litigation could be a useful variable within the data model, e.g., is the position associated with certain litigation prone risks (such as occupational hazards) and if so, to what degree? Again, direct marketing initiatives within other professional services domains (as well as by the way potentially any/all direct marketing initiatives wherein the associated potential service to be rendered or product to be sold carries with it the potential for certain recognized consumer liability risks) could benefit by implementing variations of the present invention as a screening tool (in which the variables used in the predictive litigiousness risk model are adapted appropriately to the particular domain to which it is applied). Again as in the medical case, the monetary risks associated with litigation could be weighed against the predicted monetary profits on a case by case basis.

What is claimed:

1. A system that determines risk profiles of patients for potential for litigiousness against physicians providing or considered for providing service to the patients, comprising:
   a database configured to store information identifying patients and physicians as well as litigation information relating to the patients and physicians; and
   a computer configured to execute a risk assessment module that calculates a litigation risk profile for a designated patient of a physician as a function of the information stored in the database relating to the designated patient's past litigation history and values of variables used to predict the likelihood of future litigious activities by the designated patient of the physician based upon past behavior derived using data mining techniques from the information collected about the designated patient of the physician, and an interface that facilitates the input into the database of information identifying patients, physicians, and litigation information relating to the patients and/or physicians, that facilitates the query of the information stored in the database, and that displays the calculated litigation risk profiles.

2. A system as in claim 1, wherein the database stores patient data, and the interface includes patient management software that queries the database for information regarding a potential patient and displays the calculated litigation risk profile of the potential patient.

3. A system as in claim 2, wherein the database includes patient records including previous litigation history and/or insurance claims of the patient for medical services previously rendered.

4. A system as in claim 2, wherein the database includes records of doctors that refer potential patients, said doctors' records including information relating to malpractice cases previously or currently being faced by the referring doctor.

5. A system as in claim 2, wherein the database includes records of lawyers' involvement in malpractice cases.

6. A system as in claim 2, wherein the database includes records of judges' involvement in malpractice cases.

7. A system as in claim 2, wherein the database includes records of expert witnesses' involvement in malpractice cases.

8. A system as in claim 2, wherein the risk assessment module includes software that calculates the litigation risk profile for a potential patient, the litigation risk profile including a probability of a lawsuit for treatment of a particular condition and/or a predicted dollar amount of a monetary recovery for any ensuing lawsuit.

9. A system as in claim 2, wherein the risk assessment module includes software that calculates the litigation risk profile for a potential patient, the litigation risk profile including a probability of a lawsuit for treatment of a particular condition and/or an effect such a lawsuit would have on a designated doctor's insurance premiums.

10. A system as in claim 1, wherein the risk assessment module includes a logit regression that generates a value indicative of said litigation risk profile for the designated patient.

11. A system as in claim 1, wherein the values of the variables are derived from information stored in the database relating to at least one of the designated patient's medical history, socioeconomic status, demographics, and history of insurance fraud.

12. A system as in claim 1, wherein the risk assessment module calculates the litigation risk profile for the designated patient by applying a rule based filter and/or a statistical model to the information stored in the database relating to the designated patient.

13. A method of determining risk profiles of patients for potential for litigiousness against physicians providing or considered for providing service to the patients, comprising the steps of:
   searching a database for information relating to a potential patient that is to receive a service and/or product from a physician, said information including litigation information relating to the litigiousness of the potential patient;
   a computer calculating a litigation risk profile for the potential patient from the litigation information stored in the database, said litigation information relating to the potential patient's past litigation history and values of variables used to predict the likelihood of future litigious activities by the designated patient of the physician based upon past behavior derived using data mining techniques from the information collected about the potential patient of the physician;
   an interface facilitating a query, from a user, into the database of information identifying patients, physicians, and litigation information relating to the patients and/or physicians; and
   the computer displaying the calculated litigation risk profile.

14. A method as in claim 13, wherein the database stores patient data, and the searching step includes querying the database for information regarding the potential patient using patient management software.

15. A method as in claim 14, wherein the calculating step includes calculating the litigation risk profile for the potential patient, the litigation risk profile including a probability of a lawsuit for treatment of a particular condition and/or a predicted dollar amount of a monetary recovery for any ensuing lawsuit.

16. A method as in claim 14, wherein the calculating step includes calculating the litigation risk profile for the potential patient, the litigation risk profile including a probability of a lawsuit for treatment of a particular condition and/or an effect such a lawsuit would have on a designated doctor's insurance premiums.

17. A method as in claim 13, wherein the calculating step includes the step of calculating a logit regression that generates a value indicative of said litigation risk profile for the potential patient.

18. A method as in claim 13, wherein the values of the variables are derived from information stored in the database relating to at least one of the potential patient's medical history, socioeconomic status, demographics, and history of insurance fraud.

19. A method as in claim 13, wherein calculating the litigation risk profile comprises applying a rule based filter and/or a statistical model to the information stored in the database relating to the potential patient.

* * * * *